(12) United States Patent
Den et al.

(10) Patent No.: US 9,066,704 B2
(45) Date of Patent: Jun. 30, 2015

(54) X-RAY IMAGING APPARATUS

(75) Inventors: Toru Den, Tokyo (JP); Kimiaki Yamaguchi, Tokyo (JP); Chidane Ouchi, Utsunomiya (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 302 days.

(21) Appl. No.: 13/416,339

(22) Filed: Mar. 9, 2012

(65) Prior Publication Data

US 2012/0236988 A1    Sep. 20, 2012

(30) Foreign Application Priority Data

Mar. 14, 2011   (JP) ................................. 2011-055990

(51) Int. Cl.
*A61B 6/00* (2006.01)
*G01N 23/04* (2006.01)

(52) U.S. Cl.
CPC .............. *A61B 6/484* (2013.01); *G01N 23/046* (2013.01); *G01N 2223/419* (2013.01)

(58) Field of Classification Search
CPC ........ A61B 6/4291; A61B 6/484; G21K 1/06; G21K 2207/005
USPC ................................ 378/36, 62, 82
See application file for complete search history.

(56) References Cited

U.S. PATENT DOCUMENTS

| | | | |
|---|---|---|---|
| 4,969,176 A | 11/1990 | Marinus | 378/149 |
| 7,486,770 B2 | 2/2009 | Baumann et al. | 378/62 |
| 7,564,941 B2 | 7/2009 | Baumann et al. | 378/19 |
| 7,639,786 B2 | 12/2009 | Baumann et al. | 378/145 |
| 2003/0142788 A1* | 7/2003 | Cho et al. | 378/102 |
| 2007/0183583 A1* | 8/2007 | Baumann et al. | 378/145 |
| 2010/0322380 A1* | 12/2010 | Baeumer et al. | 378/62 |

FOREIGN PATENT DOCUMENTS

JP    2006-206075    8/2006

* cited by examiner

*Primary Examiner* — Glen Kao
(74) *Attorney, Agent, or Firm* — Fitzpatrick, Cella, Harper & Scinto

(57) ABSTRACT

An X-ray imaging apparatus comprises a grating configured to form an interference pattern by diffracting X-rays from an X-ray source, a amplitude grating configured to partly shield X-rays forming the interference pattern, and an X-ray detector configured to detect an intensity distribution of X-rays from the amplitude grating. The amplitude grating is comprised of a central area and a peripheral area and the peripheral area shows an X-ray transmittance higher than the central area relative to X-rays perpendicularly entering the amplitude grating.

12 Claims, 3 Drawing Sheets

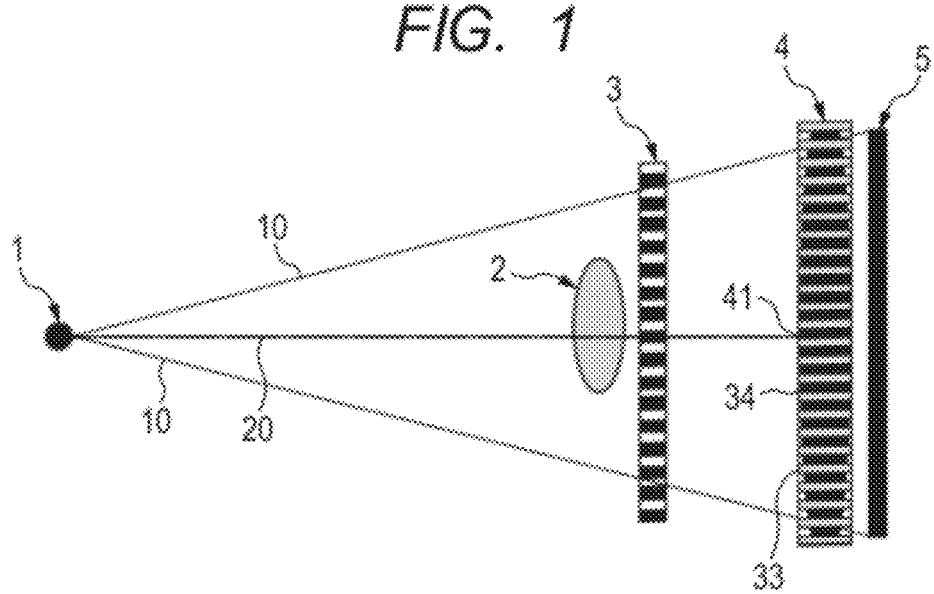

*FIG. 3*
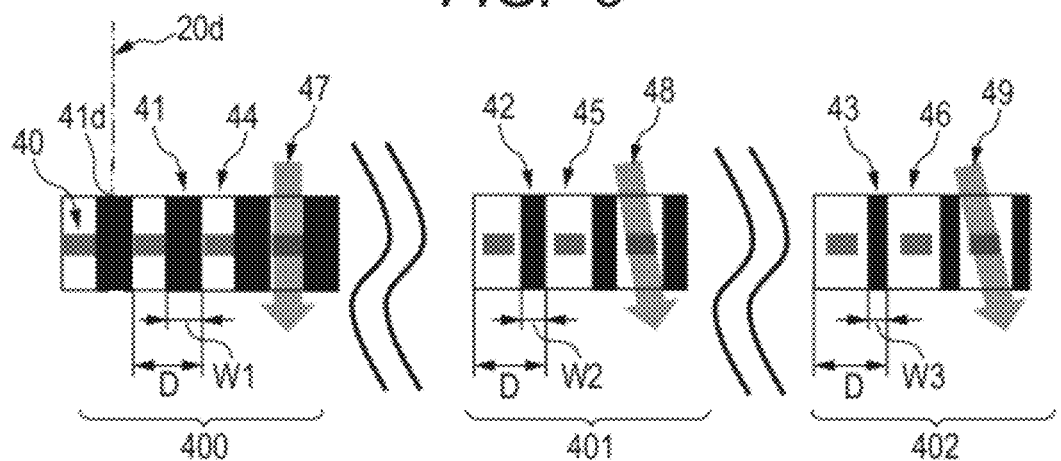
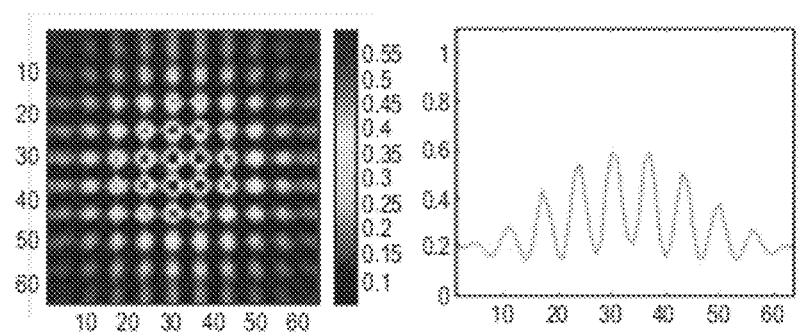
*FIG. 4A*
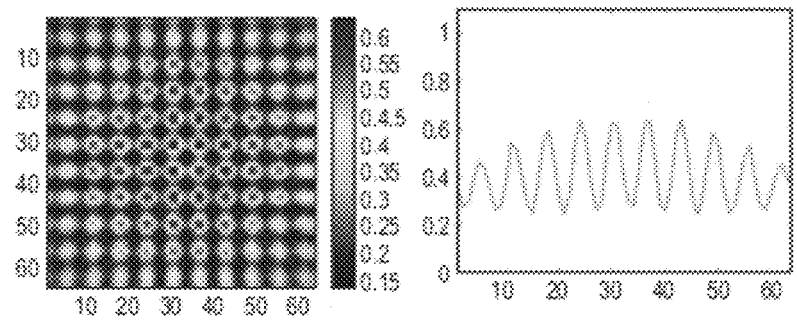
*FIG. 4B*
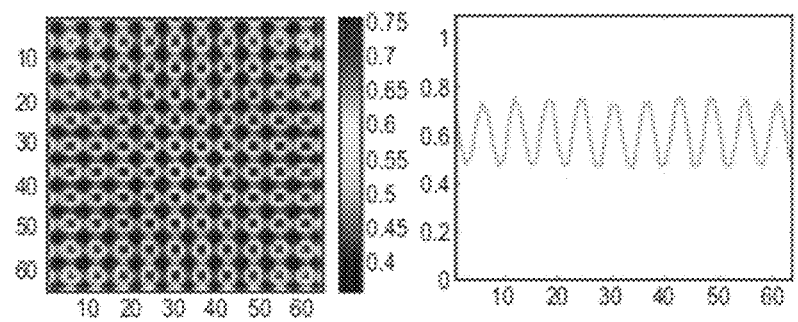
*FIG. 4C*

X-RAY IMAGING APPARATUS

BACKGROUND OF THE INVENTION

1. Field of the Invention

The present invention relates to an X-ray imaging apparatus configured to obtain an X-ray phase contrast image by means of Talbot interferometry.

2. Description of the Related Art

X-ray Talbot interferometry is known as an X-ray phase contrast imaging using phase differences of X-rays.

Talbot interferometry is a technique of reconstructing a phase image of an object from an interference pattern that appears under certain interference conditions. At least an X-ray source configured to emit spatially coherent X-rays, a grating configured to diffract the X-rays and an X-ray detector configured to detect the interference pattern (self-image) that is formed as the grating diffracts the X-rays are required to form an image of an object by means of Talbot interferometry. As an object is placed between the X-ray source and a phase grating and X-rays are irradiated onto the object, a phase shift takes place while the irradiated X-rays are transmitted through the object. The self-image that is formed while the X-rays transmitted through the object are diffracted by the grating provides phase information on the object so that a phase image of the object can be obtained by detecting and analyzing the self-image. However, since a self-image formed as a result of interference of X-rays has a very small period, X-ray detectors that are popularly being employed for imaging apparatus more often than not show an insufficient spatial resolution. Therefore, a technique of placing an amplitude grating (absorption grating), which is a grating formed by arranging X-ray transmitting portions and X-ray shielding portions, at the position (Talbot position) where the X-rays diffracted by a grating form a self-image to produce Moire fringes and detecting the produced Moire fringes is being popularly employed. Since information on the phase shift of X-rays produced by an object can be detected by way of deformed Moire fringes, an image of the object can be formed by detecting the Moire fringes by means of an X-ray detector.

When an image of an object is formed in a room such as an ordinary laboratory room, generally an X-ray tube is employed as X-ray source and an X-ray detector is placed at a position separated by only a few or several meters from the X-ray source. Therefore, X-rays are divergent X-ray beams emitted from a small source. In such a case, the parallelism between the X-ray shielding portions and the X-rays entering the amplitude grating is lost to a large extent in a peripheral area of the amplitude grating.

Then, as a result, the ratio of the X-rays that enter obliquely to the X-ray shielding portions of the amplitude grating rises particularly in the peripheral area of the amplitude grating and the contrast of intensity distribution falls in a peripheral area of the X-ray detector. To cope with this problem, Japanese Patent Application Laid-Open No. 2007-206075 (corresponding to U.S. Pat. No. 7,486,770) proposes a technique of using a curved amplitude grating or tilting the X-ray shielding portions of an amplitude grating toward an X-ray source.

SUMMARY OF THE INVENTION

Curved amplitude gratings and amplitude gratings having X-ray shielding portions tilting toward an X-ray source as described in Japanese Patent Application Laid-Open No. 2007-206075 are difficult to be prepared.

In view of the above-identified problem, therefore, the object of the present invention is to provide an X-ray imaging apparatus capable of showing an improved X-ray transmittance in a peripheral area of its amplitude grating without curving the amplitude grating or tilting the X-ray shielding portions of the amplitude grating toward an X-ray source.

According to the present invention, the object of the invention can be achieved by providing an X-ray imaging apparatus configured to image of an object, the apparatus comprising; a grating configured to form an interference pattern by diffracting X-rays from an X-ray source, an amplitude grating configured to partly shield X-rays forming the interference pattern, and an X-ray detector configured to detect an intensity distribution of X-rays from the amplitude grating, wherein the amplitude grating is comprised of a central area and a peripheral area, the peripheral area showing an X-ray transmittance higher than the central area where X-rays incident perpendicularly to the amplitude grating, where the central area is a region of a plane of the amplitude grating having a distance smaller than a predetermined value from a center of the amplitude grating while the peripheral area is a region of the plane having a distance greater than the predetermined value from the center, the center being defined as an intersection of a perpendicular drawn from the X-ray source to the plane of the amplitude grating and the plane.

Other aspects of the present invention will become apparent from the description of embodiments of the present invention given below by referring to the accompanying drawings.

BRIEF DESCRIPTION OF THE DRAWINGS

FIG. 1 is a schematic illustration of an X-ray imaging apparatus according to an embodiment of the present invention.

FIG. 2A is a schematic illustration of the amplitude grating of the embodiment, whose X-ray shielding portions are made to show varied thicknesses.

FIG. 2B is another schematic illustration of the amplitude grating of the embodiment, whose X-ray shielding portions are made to show varied thicknesses in a manner different from FIG. 2A.

FIG. 2C is still another schematic illustration of the amplitude grating of the embodiment, whose X-ray shielding portions are made to show varied thicknesses in a manner different from FIG. 2A and FIG. 2B.

FIG. 3 is a schematic illustration of the amplitude grating of the embodiment, whose X-ray shielding portions are made to show varied widths.

FIG. 4A is a simulated illustration of some of the results obtained in Reference Example.

FIG. 4B is a simulated illustration of some of the results obtained in Reference Example.

FIG. 4C is a simulated illustration of some of the results obtained in Reference Example.

DESCRIPTION OF THE EMBODIMENTS

Figure 5:
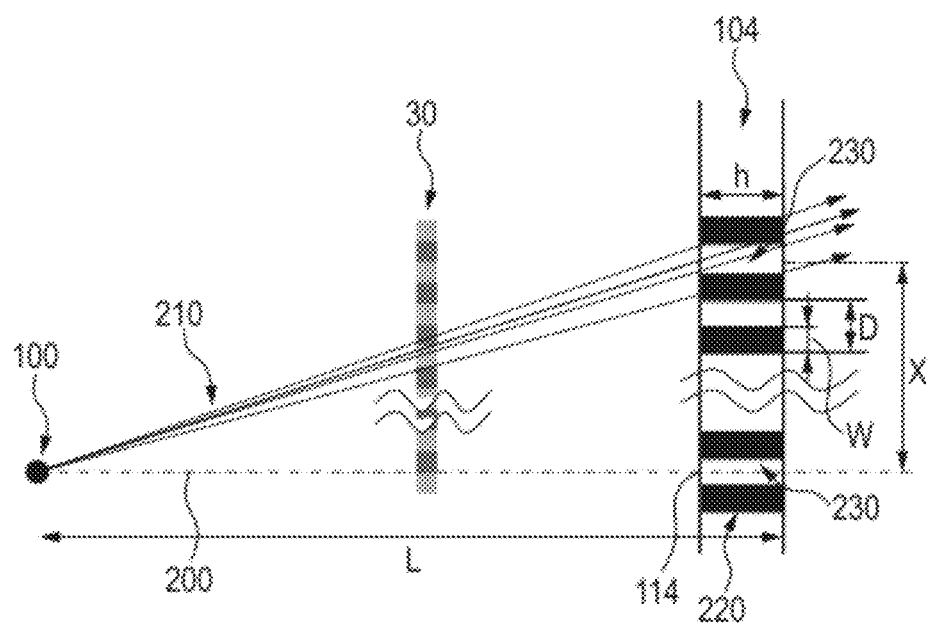
FIG. 5 is a schematic illustration of a known X-ray imaging apparatus, illustrating the relationship between the angle of incidence of X-rays to its amplitude grating and the X-ray transmittance of the amplitude grating.

Now, an embodiment of the present invention will be described in greater detail.

Exemplar configurations of the X-ray imaging apparatus of this embodiment will be described by referring to FIGS. 1, 2A through 2C and 3.

In FIG. 1 illustrating the X-ray imaging apparatus, there are shown an X-ray source 1, an object 2, a grating that is a phase grating 3, an amplitude grating 4 and an X-ray detector 5 configured to detect the intensity distribution of the X-rays transmitted through the amplitude grating.

The phase grating 3, the amplitude grating 4 and the X-ray detector 5 are arranged in such a way that X-rays enter perpendicularly the center of the X-ray irradiation area of each of them. The phase grating 3, the amplitude grating 4 and the X-ray detector 5 are arranged in parallel with each other.

While the X-ray imaging apparatus of this embodiment employs a phase grating that modulates phases as grating, an X-ray imaging apparatus according to the present invention is only required to generate Talbot interferences and hence an amplitude grating that modulates amplitudes may alternatively be employed.

Note, however, a phase grating is preferably employed as grating from the viewpoint of efficiency of utilization of X-rays.

An interference pattern (self-image) is formed by the phase grating 3 at a downstream position separated from the phase grating by the Talbot distance, for representative example. While the period of self-image depends on the magnification of the X-ray irradiation system defined by the divergence of X-rays and the shape of the phase grating, the period is generally between 1 and 15 μm.

The self-image pattern is a one-dimensional or two-dimensional bright and dark pattern depending on the shape of the phase grating. While an instance where the self-image pattern is a one-dimensional pattern is described here, this embodiment is equally applicable to an instance where the self-image pattern is a two-dimensional pattern.

When an X-ray detection area sensor is employed for the X-ray detector 5, the pixel size of the X-ray detection area sensor is generally not smaller than tens of several μm and hence the sensor cannot directly recognize the self-image. For this reason, portions of the self-image, e.g., bright portions, are shielded by the amplitude grating and only dark portions are guided to the detection device to make imaging possible.

The amplitude grating 4 has a structure formed by arranging X-ray transmitting portions 33 and X-ray shielding portions 34. The X-ray shielding portions are made of a material showing a low X-ray transmissivity. The length of the X-ray shielding portions in the direction parallel to the center axis 20 is referred to as the thickness of the X-ray shielding portions, while the length of each of the X-ray shielding portions in the direction orthogonal to the center axis 20 is referred to as the width of the X-ray shielding portions. Also note that the perpendicular drawn from the grating surface of the amplitude grating 4 (the surface at the side of the X-ray source) to the X-ray source 1 is defined as the center axis and the intersection of the center axis 20 and the grating surface of the amplitude grating is defined as the center 41 of the amplitude grating.

Examples of phase reconstruction method for acquiring phase information on an object include the fringe scanning method (phase shift method) and the Fourier transform method. With the fringe scanning method, phase information of an object is computationally acquired by detecting images for several times, shifting the relative positions between the self-image and the amplitude grating 4. With the Fourier transform method, Moire fringes are formed by means of the self-image and the amplitude grating and X-ray images are detected for once or more. Then, phase information of an object is computationally acquired from the obtained pattern. The fringe scanning method, the Fourier transform method and other methods can equally be used for this embodiment as phase reconstruction method.

A known X-ray imaging apparatus will be described here by referring to FIG. 5 for the purpose of comparison with this embodiment. As shown in FIG. 5, the direction of incident X-rays 210 runs in parallel with the X-ray transmitting portions 230 of the amplitude grating 104 at the center 114 of the amplitude grating that is the intersection of the center axis 200 and the amplitude grating 104. Thus, an image showing a good contrast can be obtained at the center of the detector. Note that the center of the detector refers to the intersection of the perpendicular drawn from the X-ray source to the X-ray receiving surface of the detector and the X-ray receiving surface. X-rays transmitted through the center 114 of the amplitude grating enter the center of the detector.

However, the direction of incident X-rays 210 does not run in parallel with the X-ray transmitting portions 230 of the amplitude grating 104 in a peripheral area of the amplitude grating 104 so that X-rays that need to be transmitted are shielded there. If the pitch of arrangement of the X-ray shielding portions 220 is D and the width and the thickness of X-ray shielding portion 220 are w and h respectively, while the distance from the X-ray source 100 to the X-ray detector is L and the distance from the center of the amplitude grating on the grating surface of the amplitude grating is x, then in a peripheral area of the amplitude grating where the distance from the center of the amplitude grating is greater than the distance x expressed by $$x = L(D-w)/h,$$

the X-rays that once enter any of the X-ray transmitting portions on the grating surface enter any of the X-ray shielding portions 220 at least once before they are transmitted through and leave the amplitude grating. Then, the intensity of X-rays that are transmitted through the amplitude grating becomes lower than the intensity of X-rays transmitted through the center 114 of the amplitude grating and hence the intensity of the former X-rays also falls when they enter the X-ray detector. Thus, the signal intensity of the detector falls and, as a result, the S (signal)/N (noise) ratio falls so that phase information may be acquired with difficulty.

Differently stated, the intensity of X-rays transmitted through the amplitude grating and S/N ratio are gradually reduced as a function of the distance from the center of the amplitude grating and accordingly the signal intensity at the X-ray detector representing the results of detection by the X-ray detector is also reduced as a function of the distance from the center of detector.

The amplitude grating 4 of the X-ray imaging apparatus of this embodiment makes the rate of X-ray transmission in a peripheral area of the amplitude grating 4 close to the rate of X-ray transmission at the center 41 of the amplitude grating. For the purpose, the amplitude grating 4 of this embodiment has such a structure that the average value of X-ray transmittance is made greater in a peripheral area of the amplitude grating than in a central area of the amplitude grating relative to X-rays entering the amplitude grating perpendicularly. Note that the central area of the amplitude grating refers to a region where the distance from the center 41 of the amplitude grating is smaller than a predetermined value, whereas the peripheral area of the amplitude grating refers to a region where the distance from the center 41 of the amplitude grating is greater than a predetermined value. Any value may be selected for the predetermined value. As described above, when the X-ray shielding portions have a thickness and a width that are same and identical both in the central area and in the peripheral area of the amplitude grating, in a region of the amplitude grating where the distance from the center of the amplitude grating is greater than the distance x expressed by the above formula, the X-rays that once enter the region enter any of the X-ray shielding portions at least once. Therefore, the predetermined distance is preferably not greater than x. When the predetermined distance is not greater than x, the peripheral area of the amplitude grating is a region where the distance from the center of the amplitude grating is not smaller than x.

In the prior art apparatus described above by referring to FIG. 5, the amount of transmitted X-rays and S/N ratio are reduced in a region where the distance from the center of the amplitude grating is x/2 if compared with the center of the amplitude grating. For this reason, the above-described predetermined distance is preferably not greater than x/2. When the predetermined distance is not greater than x/2, the peripheral area of the amplitude grating is a region where the distance from the center of the amplitude grating is not smaller than x/2.

For this embodiment, roughly speaking, a structure that improves the transmittance of X-rays and S/N ratio of the amplitude grating 4 in the peripheral area of the amplitude grating may be a structure where the X-ray shielding portions are made less thick in the peripheral area than in the central area or a structure where the X-ray shielding portions are made narrower in the peripheral area than in the central area. In the case of this embodiment where at least either the thickness or the width of the X-ray shielding portion is made variable in the amplitude grating, the width and the thickness of the X-ray shielding portion located closest to the center of the amplitude grating are expressed respectively by w and h. The X-ray shielding portion located closest to the center of the amplitude grating refers to the X-ray shielding portion located at the center of the amplitude grating if such an X-ray shielding portion exists or to the X-ray shielding portion showing the smallest distance from the center of the amplitude grating if an X-ray transmitting portion is located at the center of the amplitude grating.

Now, a structure of the amplitude grating where the X-ray shielding portions are made less thick in the peripheral area than in the central area will be described below by referring to FIGS. 2A through 2C. In the amplitude gratings shown in FIGS. 2A through 2C, the thickness of X-ray shielding portion is continuously reduced as a function of the distance from the center of the amplitude grating. Thus, regardless of the boundary dividing the central area and the peripheral area of the amplitude grating, the average thickness of the X-ray shielding portions arranged in the peripheral area of the amplitude grating is smaller than the average thickness of the X-ray shielding portions arranged in the central area of the amplitude grating.

In the alternative amplitude gratings 4 (4a, 4b, 4c) shown in FIGS. 2A through 2C, X-ray shielding portions 32 (32a, 32b, 32c) and X-ray transmitting portions 33 (33a, 33b, 33c) are arranged. The X-ray shielding portions 32 are preferably made of a heavy element. For example, the material of the X-ray shielding portions 32 may be selected from gold, lead, bismuth or alloys containing any of them. On the other hand, the X-ray transmitting portions 33 are preferably made of a light element. For example, the material of the X-ray transmitting portions 33 may be selected from Si, Al, C, Mg or materials containing any of them. In each of FIGS. 2A through 2C, the upper side is the side of the X-ray source and the lower side is the side of the X-ray detector. In each of FIGS. 2A through 2C, the center axis 20 (20a, 20b, 20c) of the amplitude grating and the intersection 41 (41a, 41b, 41c) of the center axis of the amplitude grating are shown at the center.

The amplitude grating 4a shown in FIG. 2A is an instance where the thickness of X-ray shielding portion is reduced both from the top and from the bottom as a function of the distance from the center 41a of the amplitude grating.

The amplitude grating 4b shown in FIG. 2B is an instance where the thickness of X-ray shielding portion is reduced from the top as a function of the distance from the center 41b of the amplitude grating.

The amplitude grating 4c shown in FIG. 2C is an instance where the thickness of X-ray shielding portion is reduced from the bottom as a function of the distance from the center 41c of the amplitude grating.

In the amplitude grating 4c, an X-ray transmitting member 34 is fitted to the bottom of each of the X-ray shielding portions and the thickness of X-ray transmitting member 34 increases as a function of the distance from the center 41c of the amplitude grating.

With Talbot interferometry of placing an amplitude grating at a position where a self-image is to be formed for forming an image, the thickness of X-ray shielding portion is generally preferably large in the amplitude grating because a large thickness can effectively shield X-rays. However, in the instances of amplitude grating shown in FIGS. 2A through 2C, the rate of X-ray transmission in a peripheral area of the amplitude grating is made close to the rate of X-ray transmission at the center of the amplitude grating by reducing the thickness of X-ray shielding portion as a function of the distance from the center of the amplitude grating.

As for the methods of preparing the above-described amplitude gratings, an amplitude grating as shown in FIG. 2B can be prepared by forming a mold, employing an Si substrate and a semiconductor or a MEMS process, and subsequently filling the mold with Au by plating so as to make Au adhere with a thickness that decreases as a function of the distance from the center. An amplitude grating shown in FIG. 2C can be prepared by forming a mold, employing an Si substrate and a semiconductor process, subsequently filling the mold with Ni by plating so as to make Ni adhere to the peripheral area with a thickness that increases as a function of the distance from the center and then filling Au on the Ni by plating. Ni shows a higher X-ray transmissivity than Au because Ni is a lighter element if compared with Au.

While the thickness of X-ray shielding portion is continuously reduced as a function of the distance from the center in each of the amplitude gratings shown in FIGS. 2A through 2C, the thickness may alternatively discontinuously be reduced. For example, the thickness may be reduced stepwise.

Now, a structure where the X-ray shielding portions are made less wide will be described below by referring to FIG. 3. In FIG. 3, the center axis 20d and the center 41d of the amplitude grating are shown at the left and a part of the amplitude grating having the longest distance from the center 41d is shown at the right, a part of the peripheral area being shown at the center.

In the amplitude grating shown in FIG. 3, the width of X-ray shielding portion is continuously decreased as a function of the distance from the center of the amplitude grating. Therefore, regardless of the boundary dividing the central area and the peripheral area of the amplitude grating, the average width of the X-ray shielding portions arranged in the peripheral area of the amplitude grating is smaller than the average width of the X-ray shielding portions arranged in the central area of the amplitude grating.

In FIG. 3, X-rays 47 entering a part located close to the center of the amplitude grating (a central area of the amplitude grating) are perpendicular relative to the surface of the amplitude grating, or parallel to the direction of the thickness of X-ray shielding portion 41. However, X-rays 48 entering a part 401 of the peripheral area of the amplitude grating are inclined relative to the direction of the thickness of X-ray shielding portion 42. Furthermore, X-rays 49 entering the end part 402 of the peripheral area located remotest from the center of the amplitude grating and hence separated from the center by a longer distance than the part 401 are further inclined relative to the direction of the thickness of X-ray shielding portion 43.

Differently stated, the angle formed by the direction in which X-rays 49 enter the end part 402 of the peripheral area of the amplitude grating and the direction of the thickness of X-ray shielding portion 43 is larger than the angle formed by the direction in which X-rays 48 enter the part 401 of the peripheral area of the amplitude grating and the direction of the thickness of X-ray shielding portion 42.

While the pitch D of arrangement of X-ray shielding portions and the thickness of X-ray shielding portion are same in the central area 400, in the part 401 and in the end part 402 of the amplitude grating, the width of X-ray shielding portion is reduced as a function of the distance from the center of the amplitude grating.

For example, while the width w1 of the X-ray shielding portions 41 in the central area 400 of the amplitude grating is a half of the pitch D of arrangement of X-ray shielding portions, or D/2, (and hence the width of the X-ray transmitting portions 44 there is D/2), the width w2 of the X-ray shielding portions 42 in the part 401 of the peripheral area of the amplitude grating is D/3 (and hence the width of the X-ray transmitting portions 45 there is 2D/3) and the width w3 of the X-ray shielding portions in the end part 402 of the peripheral area of the amplitude grating is D/4 (and hence the width of the X-ray transmitting portions 46 there is 3D/4).

As the width of X-ray shielding portion is reduced as a function of the distance from the center 41d of the amplitude grating, part of X-rays entering the amplitude grating are transmitted through the amplitude grating without entering any of the X-ray shielding portions. Due to this arrangement, the intensity of the X-rays transmitted through the part 401 of the peripheral area of the amplitude grating and the intensity of the X-rays transmitted through the end part 402 of the peripheral area of the amplitude grating come close to the intensity of the X-rays transmitted through the central area 400 of the amplitude grating so that the amplitude of the signal detected by a peripheral area of the detector is boosted if compared with Reference Example. Note that terms "peripheral area", "end part" and "part" are used in the above description and the peripheral area of the amplitude grating is a region where the distance from the center of the amplitude grating is greater than a predetermined value as described above. Thus, both the part 401 and the end part 402 are in the peripheral area of the amplitude grating.

As for the methods of preparing the above-described amplitude grating, an amplitude grating as shown in FIG. 3 can be prepared by employing, for example, an Si substrate to form a mold for producing X-ray shielding portions having a width that is narrowed as a function of the distance from the center of the amplitude grating and subsequently filling the mold with Au by plating. The width of X-ray shielding portion may be continuously or discontinuously reduced as a function of the distance from the center of the amplitude grating.

With the above-described arrangement of this embodiment, the reduction of the X-ray dose in the peripheral area of the amplitude grating due to divergence of X-rays from a point X-ray source can be suppressed and hence the reduction of the signal intensity at a peripheral area of the X-ray detector can also be suppressed. While two different techniques for improving the transmittance of X-rays in a peripheral area of an amplitude grating are described above, both the technique of reducing the thickness of X-ray shielding portion and the technique of reducing the width of X-ray shielding portion can basically provide a similar effect.

The two techniques may be combined for use. The amplitude grating may not necessarily be flat-plate shaped and may alternatively be curved. However, with the above-described techniques of this embodiment, the dose of X-rays transmitted through a peripheral area of an amplitude grating can be made to come close to that of X-rays transmitted through a central area of the amplitude grating even when the amplitude grating is not so curved as is along the wave front of X-rays.

Now, the present invention will be described further by way of examples.

Example 1

In Example 1, numerical calculations were conducted on an exemplar X-ray imaging apparatus in which the thickness of X-ray shielding portion was reduced as a function of the distance from the center of the amplitude grating of the apparatus in a manner as described above by referring to FIG. 2A. The configuration of the imaging apparatus is same as the one illustrated in FIG. 1. In other words, the imaging apparatus includes an X-ray source, a phase grating, an amplitude grating and an X-ray detector.

The energy level of X-rays from the X-ray source was 17.5 KeV and a one-dimensional phase grating was used for the phase grating, while a one-dimensional amplitude grating with a pitch of 9.6 μm was used for the amplitude grating.

In the amplitude grating, the X-ray shielding portion located closest to the center of the amplitude grating had a thickness of 50 μm and a width of 4.8 μm.

The distance from the X-ray source to the X-ray detector was 120 cm.

With the above-described conditions, the distance x is 11.5 cm. In other words, a region showing a distance to the center of the amplitude grating not less than 11.5 cm was specified as peripheral area. In the case of ordinary prior art amplitude gratings, where the thickness of the X-ray shielding portions arranged in the amplitude grating is uniformly 50 μm, the X-rays that enter the peripheral area of the amplitude grating enter any of the X-ray shielding portions at least once. Then, as a result, the intensity of the X-rays is reduced and hence the amplitude of the signal detected by the detector is also reduced.

In this example, the thickness of the X-ray shielding portion located at the position separated from the center of the amplitude grating by 11.5 cm is made equal to 40, 30, 20, 15, 10 and 5 μm. Then, the amplitude of the signal of the self-image detected by the detector is correspondingly about 2.1 times, 3.1 times, 3.9 times, 4.1 times, 4.1 times and 3.1 times greater than the amplitude of the signal that is obtained when the thickness of the X-ray shielding portion is 50 μm.

While the signal base line rises, the signal amplitude also rises. Particularly, in the case of this example, the signal amplitude remarkably rises when the thickness of the X-ray shielding portion at the above-identified position is about 10 to 20 μm if compared with the instance where the thickness is 50 μm.

The transmittance of X-rays (with an energy level of 17.5 KeV) is about 12% when the Au is 10 μm thick, about 4% when the Au is 15 μm thick, about 1.4% when the Au is 20 μm thick and about 65% when the Au is 5 μm thick.

The effect of the above-described embodiment can be achieved when the transmittance of X-rays entering the X-ray shielding portions perpendicularly is raised to about 65%. Therefore, the transmittance of X-rays perpendicularly entering the X-ray shielding portion separated from the center of the amplitude grating by distance x is preferably not greater than 65% and not smaller than 1.4%. Additionally, the transmittance of X-rays perpendicularly entering the X-ray shielding portion separated form the center of the amplitude grating by distance x is preferably not greater than 12%.

The numerical calculations of this example were conducted by assuming that an X-ray shielding portion is arranged at the position separated from the center of the amplitude grating by exactly 11.5 cm. However, if X-ray shielding portion is not arranged at the position separated from the center of the amplitude grating by exactly 11.5 cm, an effect similar to that of this example can be achieved by defining the thickness of the X-ray shielding portion located closest to the position separated from the center of the amplitude grating by 11.5 cm as in this example because of the pitch of arrangement of X-ray shielding portions is small.

Example 2

In Example 2, numerical calculations were conducted on an exemplar X-ray imaging apparatus in which the width of X-ray shielding portion was reduced as a function of the distance from the center of the amplitude grating of the apparatus in a manner as described above by referring to FIG. 3.

The configuration of the X-ray imaging apparatus of this example is same as that of the apparatus of Example 1 except the amplitude grating.

In this example, the width of the X-ray shielding portion located at the position separated from the center of the amplitude grating by 11.5 cm is reduced from 4.8 μm to 3.8, 2.9, 1.9, 1.4, 1.0 and 0.5 μm. Then, the amplitude of the signal of the self-image detected by the detector is correspondingly about 2.1 times, 3.1 times, 3.9 times, 4.1 times, 4.1 times and 3.1 times greater than the amplitude of the signal that is obtained when the width of the X-ray shielding portion is 4.8 μm.

While the signal base line rises, the signal amplitude also rises if compared with the instance where the width of the X-ray shielding portion is 4.8 μm. When, for example, the width of the X-ray shielding portion is 0.5 μm and 2.9 μm, the signal amplitude is more than three times of the signal amplitude observed when the width of the X-ray shielding portion is 4.8 μm. Thus, the effect of the above-described embodiment can be achieved when the width of X-ray shielding portion in the peripheral area of the amplitude grating is not greater than 80% and not smaller than 10% of the width of X-ray shielding portion in the central area of the amplitude grating.

Particularly, in this example, the signal amplitude remarkably rises when the width of X-ray shielding portion is about 1 to 2 μm. Therefore, the width of X-ray shielding portion in the peripheral area of the amplitude grating is preferably not greater than about 40% and not smaller than about 20% of the width of X-ray shielding portion in the central area of the amplitude grating.

Reference Example

In this reference example, the relationship between the thickness of X-ray shielding portion of the amplitude grating and the outcome of detection by the X-ray detector configured to detect X-rays transmitted through the amplitude grating was looked into. The obtained results will be described below by referring to FIGS. 4A through 4C.

The configuration of the X-ray imaging apparatus of this reference example is basically same as that of the apparatus of Example 1 but the distance between the X-ray source and the X-ray detector was made to be equal to 112 cm and the X-ray energy level was made to be equal to 30 keV, while the pitch of the amplitude grating was made equal to 3.7 μm in this reference example. Additionally, the phase grating and the amplitude grating of this reference example are two-dimensional gratings showing a two-dimensional periodic structure and the amplitude grating shows a lattice-like pattern.

The X-ray shielding portions of the amplitude grating were made of Au and three amplitude gratings including an amplitude grating having X-ray shielding portions showing a uniform thickness of 60 μm throughout the amplitude grating, an amplitude grating having X-ray shielding portions showing a uniform thickness of 40 μm throughout the amplitude grating and a amplitude grating having X-ray shielding portions showing a uniform thickness of 20 μm throughout the amplitude grating were used. FIGS. 4A through 4C schematically illustrate the Moire fringes and the cross sectional intensity profiles thereof detected by the X-ray detector.

In each of FIGS. 4A through 4C, the Moire fringes detected by the detector is shown at the left side and the cross sectional intensity profile thereof is shown at the right side.

FIG. 4A shows the Moire fringes and the cross sectional intensity profile thereof detected when an amplitude grating having X-ray shielding portions of a thickness of 60 μm was employed. Similarly, FIG. 4B shows the Moire fringes and the cross sectional intensity profile thereof detected when an amplitude grating having X-ray shielding portions of a thickness of 40 μm was employed and FIG. 4C shows the Moire fringes and the cross sectional intensity profile thereof detected when an amplitude grating having X-ray shielding portions of a thickness of 20 μm was employed.

As seen from FIGS. 4A through 4C, in the case of using an amplitude grating having a two-dimensional periodic structure too, the signal amplitude of the Moire fringes in the peripheral area of the detector rises and comes close to the signal amplitude of the Moire fringes in the central area of the detector. However, at the same time, the signal amplitude of the Moire fringes falls in the central area of the detector when the thickness of X-ray shielding portion is reduced as equally seen from FIGS. 4A through 4C. Thus, the X-ray imaging apparatus of the above-described embodiment and those of the above-described examples are effective for raising the signal amplitude in the peripheral area of the detector while suppressing the fall of the signal amplitude in the central area of the detector.

Note that X-ray transmittance of the amplitude grating of this reference example was 4, 12 and 35% respectively for the Au thickness of 60, 40 and 20 μm when X-rays are made to perpendicularly enter the X-ray shielding portions.

While the present invention is described above by way of an exemplary embodiment, the present invention is by no means limited to the above-described embodiment, which may be modified and altered in various different ways without departing from the spirit and scope of the invention.

This application claims the benefit of Japanese Patent Application No. 2011-055990, filed Mar. 14, 2011, which is hereby incorporated by reference herein in its entirety.

What is claimed is:

1. An X-ray apparatus configured to acquire information on an object, the apparatus comprising:
a grating configured to form an interference pattern by diffracting X-rays from an X-ray source;
an amplitude grating configured to partly shield X-rays forming the interference pattern, the amplitude grating having a plurality of shielding portions arranged therein for shielding X-rays, comprising a center, and including a central area and a peripheral area, the center being a point located on the amplitude grating where a hypothetical straight line connecting the X-ray source and the amplitude grating intersects with the amplitude grating perpendicularly thereto, the central area being an area where a distance from any point located therein to the center is smaller than a predetermined length, and the peripheral area being an area where a distance from any point located therein to the center is not smaller than the predetermined length; and an X-ray detector configured to detect an intensity distribution of X-rays from the amplitude grating, wherein each of the shielding portions has a thickness in the direction perpendicular to the direction of arrangement of the plurality of shielding portions, the thicknesses of the shielding portions that are arranged in the central area having a first average thickness and the thicknesses of the shielding portions that are arranged in the peripheral area having a second average thickness which is smaller than the first average thickness.

2. The X-ray apparatus according to claim 1, wherein each of the plurality of shielding portions has a width in the direction of arrangement of the shielding portions, and the predetermined length is a value x expressed by the formula:

$$x=L(D-w)/h$$

where L represents a distance from the X-ray source to the amplitude grating and D represents a pitch of arrangement of the plurality of shielding portions while w and h represent the width and the thickness, respectively, of the shielding portion located closest to the center.

3. The X-ray apparatus according to claim 2, wherein the thickness of the shielding portion having a distance from the center of the amplitude grating that is closest to the value x among the shielding portions arranged in the peripheral area of the amplitude grating is such that the transmittance of the X-rays is not greater than 65% and not smaller than 1.4% when the X-rays perpendicularly enter the shielding portion.

4. The X-ray apparatus according to claim 2, wherein the width of the shielding portion having a distance from the center of the amplitude grating that is closest to the value x among the shielding portions arranged in the peripheral area of the amplitude grating is not greater than 80% and not smaller than 10% of the width of the shielding portion located closest to the center.

5. The X-ray apparatus according to claim 1, wherein each of the shielding portions has a width in the direction of arrangement of the plurality of shielding portions, the widths of the shielding portions in the central area having a first average width while the widths of the shielding portions in the peripheral area having a second average width which is smaller than the first average width.

6. The X-ray apparatus according to claim 1, wherein the plurality of shielding portions have thicknesses which are continuously reduced as a function of the distance of a shielding portion from the center of the amplitude grating.

7. The X-ray apparatus according to claim 1, wherein the direction perpendicular to the direction of arrangement of the plurality of shielding portions agrees with the direction orthogonal to a substrate of the amplitude grating.

8. The X-ray apparatus according to claim 1, wherein the amplitude grating has a shape of flat plate.

9. The X-ray apparatus according to claim 8, wherein each of the plurality of shielding portions is oriented parallel to the hypothetical straight line.

10. An X-ray apparatus configured to acquire information on an object, the apparatus comprising:

a grating configured to form an interference pattern by diffracting X-rays from an X-ray source;

an amplitude grating configured to partly shield X-rays forming the interference pattern, the amplitude grating having a plurality of shielding portions arranged therein for shielding X-rays, comprising a center, and including a central area and a peripheral area, the center being a point located on the amplitude grating where a hypothetical straight line connecting the X-ray source and the amplitude grating intersects with the amplitude grating perpendicularly thereto, the central area being an area where a distance from any point located therein to the center is smaller than a predetermined length, and the peripheral area being an area where a distance from any point located therein to the center is not smaller than the predetermined length; and an X-ray detector configured to detect an intensity distribution of X-rays from the amplitude grating, wherein each of the shielding portions has a width in the direction of arrangement of the plurality of shielding portions, the widths of the shielding portions that are arranged in the central area having a first average width and the widths of the shielding portions that are arranged in the peripheral area having a second average width which is smaller than the first average width.

11. The X-ray apparatus according to claim 10, wherein each of the plurality of shielding portions has a thickness perpendicular to the direction of arrangement of the plurality of shielding portions, and the predetermined length is a value x expressed by the formula:

$$x=L(D-w)/h$$

where L represents a distance from the X-ray source to the amplitude grating and D represents a pitch of arrangement of the plurality of shielding portions while w and h represent the width and the thickness, respectively, of the shielding portion located closest to the center.

12. The X-ray apparatus according to claim 10, wherein the plurality of shielding portions have widths which are continuously reduced as a function of the distance of a shielding portion from the center of the amplitude grating.

\* \* \* \* \*